(12) United States Patent
Yuan

(10) Patent No.: US 12,367,982 B2
(45) Date of Patent: Jul. 22, 2025

(54) METHOD FOR DISPLAYING AN EARLY WARNING SCORE, MONITORING DEVICE AND DISPLAY SYSTEM

(71) Applicant: SHENZHEN MINDRAY BIO-MEDICAL ELECTRONICS CO., LTD., Shenzhen (CN)

(72) Inventor: Weiwei Yuan, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 600 days.

(21) Appl. No.: 17/362,792

(22) Filed: Jun. 29, 2021

(65) Prior Publication Data

US 2021/0327592 A1 Oct. 21, 2021

Related U.S. Application Data

(63) Continuation of application No. PCT/CN2018/125678, filed on Dec. 29, 2018.

(51) Int. Cl.
*G16H 50/30* (2018.01)
*A61B 5/00* (2006.01)
(Continued)

(52) U.S. Cl.
CPC ........... *G16H 50/30* (2018.01); *A61B 5/7435* (2013.01); *A61B 5/746* (2013.01); *G06T 11/206* (2013.01);
(Continued)

(58) Field of Classification Search
CPC ......... G16H 50/30; G16H 40/67; G16H 50/70
See application file for complete search history.

(56) References Cited

U.S. PATENT DOCUMENTS 10,095,838 B2 * 10/2018 Hebler ................... G16Z 99/00
2002/0010390 A1   1/2002 Guice et al.
(Continued)

FOREIGN PATENT DOCUMENTS

CN        202104912 U    1/2012
CN        105030203 A   11/2015
(Continued)

OTHER PUBLICATIONS

International Search Report issued in corresponding International Application No. PCT/CN2018/125678, mailed Sep. 30, 2019, 4 pages.

*Primary Examiner* — Joshua B Blanchette
(74) *Attorney, Agent, or Firm* — Morgan, Lewis & Bockius LLP

(57) ABSTRACT

A method for displaying an early warning score, monitoring device and display system are provided. The method includes: within a first period of time, receiving multiple physiological parameters, and obtaining a first group of physiological data; obtaining at least one first total early warning score at a first frequency; within a second period of time, receiving multiple physiological parameters, and obtaining a second group of physiological data; obtaining at least one second total early warning score at a second frequency; and along with the variation of time, sequentially outputting the at least one first total early warning score and the at least one second total early warning score. The monitoring device and system can prompt a medical staff to notice the physical condition of a patient in a timely manner, and improve the monitoring efficiency.

19 Claims, 7 Drawing Sheets

(51) Int. Cl.
*G06T 11/20* (2006.01)
*G16H 40/67* (2018.01)
*G16H 50/70* (2018.01)
*G16H 40/20* (2018.01)

(52) U.S. Cl.
CPC ............ *G16H 40/67* (2018.01); *G16H 50/70* (2018.01); *G16H 40/20* (2018.01)

(56) References Cited

U.S. PATENT DOCUMENTS

| | | | | |
|---|---|---|---|---|
| 2013/0027411 | A1* | 1/2013 | Hebler | G16H 50/30 |
| | | | | 345/501 |
| 2018/0132794 | A1* | 5/2018 | Lange | G16H 40/63 |
| 2018/0184984 | A1* | 7/2018 | Zerhusen | A61B 5/742 |
| 2020/0178903 | A1* | 6/2020 | Chaudhuri | A61B 5/7445 |

FOREIGN PATENT DOCUMENTS

| | | | | |
|---|---|---|---|---|
| CN | 206421389 | U | 8/2017 | |
| CN | 107438399 | A | 12/2017 | |
| WO | WO-2013134845 | A1 * | 9/2013 | ........... A61B 5/0022 |

\* cited by examiner

METHOD FOR DISPLAYING AN EARLY WARNING SCORE, MONITORING DEVICE AND DISPLAY SYSTEM

CROSS-REFERENCE TO RELATED APPLICATION

This disclosure is a continuation of Patent Cooperation Treaty Application No. PCT/CN2018/125678, filed on Dec. 29, 2018, which is hereby incorporated by reference in its entirety.

TECHNICAL FIELD

The present application relates to the field of medical technologies, and in particular, to a method for displaying an early warning score, a monitoring device, and a display system.

BACKGROUND

Medical staff's timely and accurate judgment of a patient's condition plays a vital role in success of carrying out timely and effective treatment on the patient and of saving the patient's life. In addition, early warning score (EWS) is a visual graphical design of EWS. The EWS is to evaluate commonly used examination indexes and give corresponding scores. For example, corresponding scores are assigned to a plurality of parameters (i.e., physiological indexes) such as body temperature, systolic blood pressure, heart rate, respiration rate, and level of consciousness, and then principles of medical treatment intervention at different levels are determined according to different scores; and once the score reaches a certain mark, an event reminder is "triggered" to remind relevant medical staff to perform corresponding medical treatment as soon as possible. When the corresponding scores are displayed based on the EWS, current scores corresponding to the parameters and actual measured values are usually displayed in the form of a digital table.

However, the above implementation method is low in monitoring efficiency.

SUMMARY

Embodiments of the present application provide a method for displaying an early warning score, a monitoring device, and a system, which can remind medical staff to pay attention to a patient's physical condition in a timely manner, and thus improve the monitoring efficiency.

In a first aspect, an embodiment of the present application provides a method for displaying an early warning score, the method comprising:

receiving a plurality of physiological parameters collected, in a first time period, from an object that is monitored in real time, so as to obtain a first set of physiological data;

acquiring at least one first total early warning score at a first frequency based on the first set of physiological data;

receiving a plurality of physiological parameters collected, in a second time period, from the object that is monitored in real time, so as to obtain a second set of physiological data;

acquiring at least one second total early warning score at a second frequency based on the second set of physiological data; and sequentially outputting the at least one first total early warning score and the at least one second total early warning score over time.

In a second aspect, an embodiment of the present application provides a monitoring device, the monitoring device comprising:

a parameter measurement circuit, which is electrically connected to a sensor accessory provided on the body of a patient, and is configured to obtain a plurality of physiological parameters; and a processor and a memory, wherein the memory is configured to store a computer program, and the processor is configured to implement the following steps when executing the computer program stored in the memory:

receiving a plurality of physiological parameters collected, in a first time period, from an object that is monitored in real time, so as to obtain a first set of physiological data;

acquiring at least one first total early warning score at a first frequency based on the first set of physiological data;

receiving a plurality of physiological parameters collected, in a second time period, from the object that is monitored in real time, so as to obtain a second set of physiological data;

acquiring at least one second total early warning score at a second frequency based on the second set of physiological data; and sequentially outputting the at least one first total early warning score and the at least one second total early warning score over time.

In a third aspect, an embodiment of the present application further provides a display system, the display system comprising a monitoring device and a wearable device, wherein the monitoring device is communicatively connected to the wearable device, and is configured to perform the method as described in the first aspect.

In a fourth aspect, an embodiment of the present application further provides a computer-readable storage medium storing a computer program, wherein the computer program comprises program instructions that, when executed by a processor, cause the processor to perform the method as described in the first aspect.

The implementation of the embodiments of the present application can make it possible to display both a first total early warning score acquired at a first frequency and a second total early warning score acquired at a second frequency; moreover, the second total early warning score acquired at the second frequency is greater than the first total early warning score acquired at the first frequency, which can clearly notify medical staff of a patient's physical changes within a preset duration, thereby effectively avoiding the need for the medical staff to manually make correspondence of historical numerical values by themselves in urgent need of relevant numerical values (such as a total EWS), and thus improving the working efficiency of the medical staff, and making it possible to significantly improve, in a timely manner, the medical staff's attention to the patient's physical condition and thus improving the monitoring efficiency of a monitoring device or a monitor.

DETAILED DESCRIPTIONS

The terms "first", "second", etc. in the specification and the claims of the present application as well as the accompanying drawings are used to distinguish different objects, rather than to describe a specific order. In addition, the terms "comprising", "having", and any variations thereof are intended to cover non-exclusive inclusion. For example, a process, a method, a system, a product, or a device that includes a series of steps or units is not limited to the listed steps or units, but optionally further includes unlisted steps or units, or optionally further includes other steps or units inherent in these processes, methods, or devices.

Figure 1:
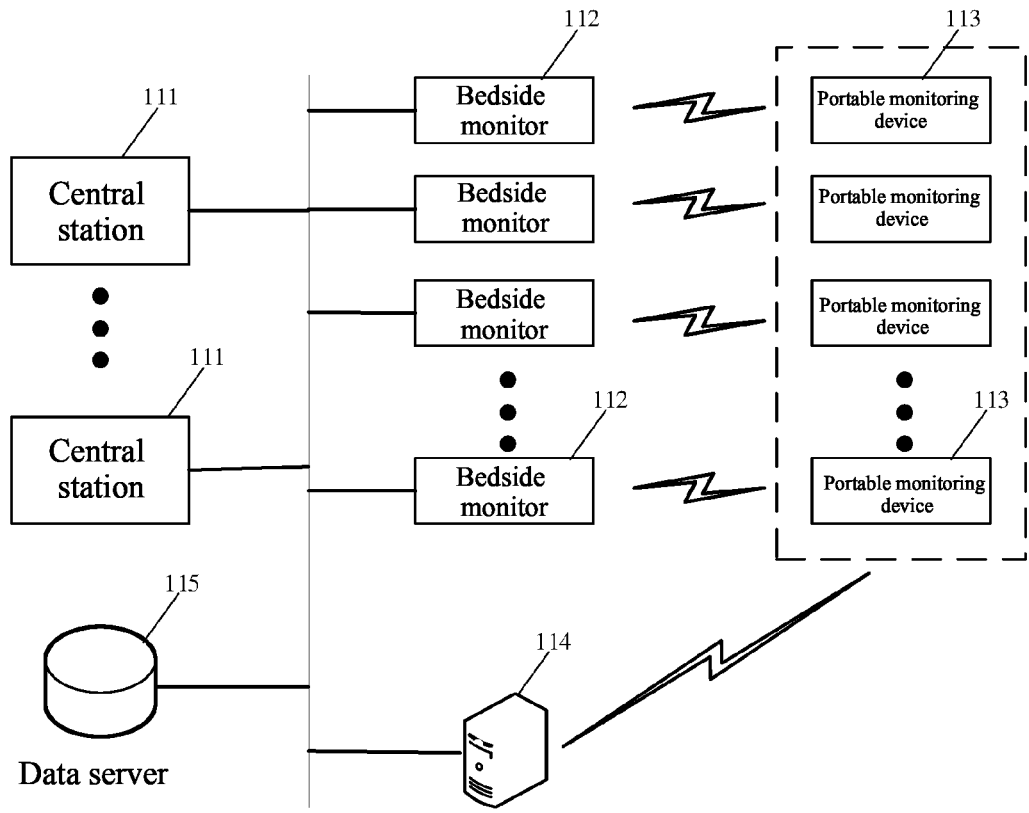
FIG. 1 is a monitor networking system used in a hospital, provided according to an embodiment of the present application.

Usually, when a patient is in hospital, it is necessary to keep an eye on a plurality of physiological parameters of the patient by means of a monitor all the time. As shown in FIG. 1, a monitor networking system used in a hospital is provided. By using the system, data of a monitor may be saved as a whole to centrally manage patient information and nursing information that are stored in association, which facilitates storage of historical data and alarming in association. In the system shown in FIG. 1, a bedside monitor 112 may be provided for each hospital bed. The bedside monitor 112 may be a multi-parameter monitor or module assembly. In addition, each bedside monitor 112 may further be paired with one portable monitoring device 113 for transmission. The portable monitoring device 113 provides a simple and portable parameter processing module, which can be worn on the body of a patient to perform mobile monitoring for the patient. After the portable monitoring device 113 and the bedside monitor 112 perform wired or wireless communication, physiological data generated through mobile monitoring may be transmitted to the bedside monitor 112 for display, or transmitted, by means of the bedside monitor 112, to a central station 111 for viewing by a doctor or a nurse, or transmitted, by means of the bedside monitor 112, to a data server 115 for storage. In addition, the portable monitoring device 113 may further directly transmit, by means of a wireless network node 114 arranged in the hospital, the physiological data generated through mobile monitoring to the central station 111 for storage and display, or transmit, by means of a wireless network node 114 arranged in the hospital, the physiological data generated through mobile monitoring to the data server 115 for storage. It can be seen that the data corresponding to the physiological parameters displayed on the bedside monitor 112 may originate from a sensor accessory directly connected to the monitor, or from the portable monitoring device 113, or from the data server.

Figure 2:
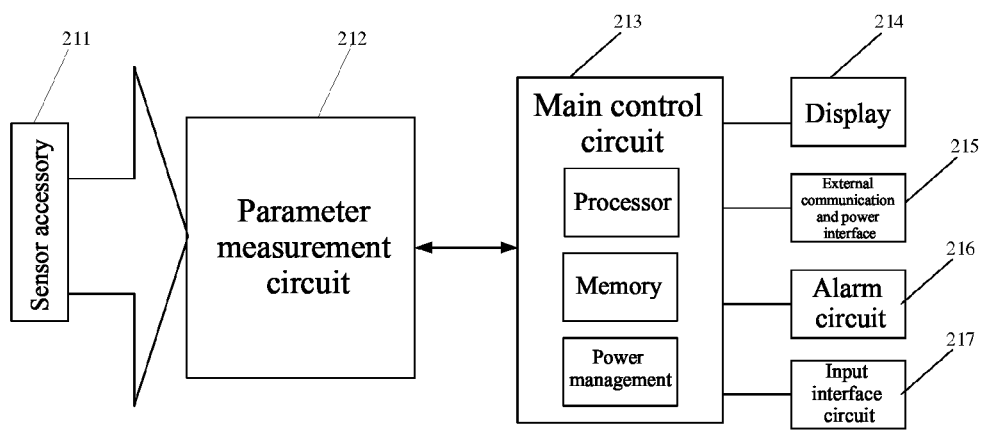
FIG. 2 is a system framework diagram of a multi-parameter monitor or module assembly provided according to an embodiment of the present application.

As shown in FIG. 2, a system framework diagram of a multi-parameter monitor or module assembly is provided. The multi-parameter monitor or module assembly comprises at least a parameter measurement circuit 212. A parameter measurement circuit 212 corresponding to at least one physiological parameter may be comprised. At least one parameter measurement circuit 212 of an electrocardiography signal parameter measurement circuit, a respiration parameter measurement circuit, a body temperature parameter measurement circuit, a blood oxygen parameter measurement circuit, a non-invasive blood pressure parameter measurement circuit, an invasive blood pressure parameter measurement circuit, etc. may be comprised. Each parameter measurement circuit 212 is connected to an externally inserted sensor accessory 211 through a corresponding sensor interface. The sensor accessory 211 comprises detection accessories corresponding to the detection of physiological parameters such as electrocardiogram, respiration, blood oxygen, blood pressure, and body temperature. The parameter measurement circuit 212 is mainly configured to be connected to the sensor accessory 211 to obtain collected physiological parameter signals, and may comprise measurement circuits for at least two types of physiological parameters. The parameter measurement circuit 212 may be, but is not limited to, a physiological parameter measurement circuit (module), a human physiological parameter measurement circuit (module), or a sensor to collect human physiological parameters, etc. Specifically, the parameter measurement circuit 212 obtains, a physiological sampled signal related to a patient from an external physiological parameter sensor accessory through an extended interface, processes the physiological sampled signal and then obtains physiological data for alarming and display. The extended interface may also be used to output, through a corresponding interface and to an external physiological parameter monitoring accessory, a control signal, regarding how to collect physiological parameters, that is output by a main control circuit, so as to implement the monitoring and control of the physiological parameters of the patient.

The multi-parameter monitor or module assembly may further comprise a main control circuit 213. The main control circuit 213 needs to comprise at least one processor and at least one memory. Certainly, the main control circuit 213 may further comprise at least one of a power management module, a power IP module, an interface conversion circuit, etc. The power management module is configured to control turning-on and turning-off of the overall machine, a power-on sequence of each power domain in a board card, charging and discharging of a battery, etc. The power IP module refers to associating a principle diagram of a power circuit unit that is frequently invoked repeatedly with a diagram of a printed circuit board (PCB), and then solidifying same into an independent power module, that is, converting an input voltage into an output voltage through a predetermined circuit, wherein the input voltage is different from the output voltage. For example, a voltage of 15 V is converted to 1.8 V, 3.3 V, or 3.8 V, etc. It can be understood that the power IP module may be single-channel or multi-channel. When the power IP module is single-channel, the power IP module can convert one input voltage to one output voltage. When the power IP module is multi-channel, the power IP module can convert one input voltage into a plurality of output voltages, and the plurality of output voltages may have the same or different voltage values, such that requirements of a plurality of electronic elements for different voltages are met at the same time; moreover, the module has fewer external interfaces, and operates in the system in such a way that a black box is decoupled from an external hardware system, thereby improving the reliability of the whole power system. The interface conversion circuit is configured to convert a signal output by a main control minimum system module (i.e., at least one processor and at least one memory in a main control circuit) into an input standard signal required by an actual external device. For example, supporting an external video transmission standard (video graphics array (VGA)) display function involves converting an RGB digital signal output by a main control CPU into a VGA analog signal, and supporting an external network function involves converting an RMII signal into a standard network differential signal.

In addition, the multi-parameter monitor or module assembly may further comprise one or more of a local display 214, an alarm circuit 216, an input interface circuit 217, and an external communication and power interface 215. The main control circuit is configured to coordinate and control board cards, circuits and devices in the multi-parameter monitor or module assembly. In the embodiment of the present application, the main control circuit is configured to control the data interaction and control signal transmission between the parameter measurement circuit 212 and a communication interface circuit, and transfer physiological data to the display 214 for display, or may receive an input user control instruction from a touch screen or a physical input interface circuit such as a keyboard and a key, and certainly, may also output a control signal regarding how to collect the physiological parameters. The alarm circuit 216 may be an acousto-optics alarm circuit. The main control circuit completes the calculation of physiological parameters, and can send the calculation results and waveforms of the parameters to a main unit (such as a main unit with a display, a PC, and a central station) through the external communication and power interface 215. The external communication and power interface 215 may be one or a combination of local area network interfaces composed of Ethernet, a token ring, a token bus, and an optical fiber distributed data interface (FDDI) as the backbone of these three networks, may also be one or a combination of wireless interfaces such as infrared, Bluetooth, wireless-fidelity (wifi), and WA/ITS communication, or may also be one or a combination of wired data connection interfaces such as an asynchronous transmission standard interface (RS232) and a universal serial bus (USB). The external communication and power interface 215 may also be one or a combination of a wireless data transmission interface and a wired data transmission interface. The main unit may be any computer device such as the main unit of the monitor, an electrocardiograph, an ultrasonic diagnosis instrument, a computer, etc., and a monitoring device can be formed by means of installing with matching software. The main unit may also be a communication device such as a mobile phone, and the multi-parameter monitor or module assembly sends, by means of a Bluetooth interface, data to the mobile phone supporting Bluetooth communication, so as to implement remote transmission of the data.

The multi-parameter monitoring module assembly may be arranged outside a monitor housing as an independent externally inserted parameter module, may be inserted into a main unit (comprising a main control board) of the monitor to form a plug-in monitor to serve as a part of the monitor, or may be connected to the main unit (comprising the main control board) of the monitor through a cable, and the externally inserted parameter module is used as an external accessory of the monitor. Certainly, the parameter processing module may also be built in the housing to be integrated with a main control module, or physically separated and arranged in the housing to form an integrated monitor.

Figure 3:
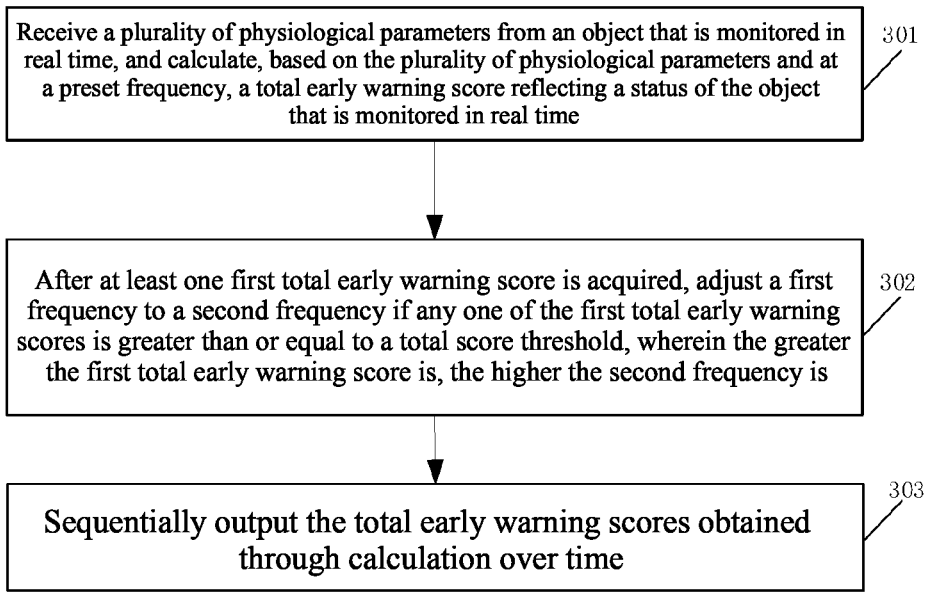
FIG. 3 is a schematic flowchart of a method for displaying an early warning score provided according to an embodiment of the present application.

FIG. 3 is a schematic flowchart of a method for displaying an early warning score provided according to an embodiment of the present application. The method for displaying an early warning score may be applied to a monitoring device. Moreover, the method may further be applied to the multi-parameter monitor or module assembly shown in FIG. 2, and the method may further be applied to the monitor networking system shown in FIG. 1, etc. A monitor is used as an example below to illustrate the method provided according to an embodiment of the present application. As shown in FIG. 3, the method for displaying an early warning score may comprise at least the steps as follows.

101. A plurality of physiological parameters are received from an object that is monitored in real time, and a total early warning score reflecting a status of the object that is monitored in real time can be calculated at a preset frequency based on the plurality of physiological parameters.

In the embodiment of the present application, the monitored object may comprise a monitored patient, etc. The preset frequency can be automatically set by a monitoring device, or manually set by medical staff, etc.

It can be understood that the frequency in the embodiment of the present application can be understood as the number of times a total early warning score is acquired in a predetermined time period (for example, per hour), etc. For example, the first frequency in the embodiment of the present application may be to acquire a total EWS (i.e., a first total early warning score) once every two hours.

For example, in one embodiment, a processor (such as a processor of a monitor) receives a plurality of physiological parameters collected, in a first time period, from an object that is monitored in real time, so as to obtain a first set of physiological data; the processor acquires at least one first total early warning score at a first frequency based on the first set of physiological data; the processor receives a plurality of physiological parameters collected, in a second time period, from the object that is monitored in real time, so as to obtain a second set of physiological data; and the processor acquires at least one second total early warning score at a second frequency based on the second set of physiological data. The first frequency may be the same as or different from the second frequency.

The first time period is continuous with the second time period along the timeline. In one of the embodiments, the first time period is neither the same as nor overlaps with the second time period.

In one of the embodiments, the monitor collects physiological parameter signals by a sensor accessory 211 attached to the body of a monitored object, for use in obtaining a plurality of physiological parameters. For example, the plurality of physiological parameters may be at least two physiological parameters of body temperature (Temp), diastolic blood pressure, systolic blood pressure (BP-S), heart rate (HR), respiration rate (RR), level of consciousness, blood oxygen (SpO2), oxygen concentration (Supp.O2), an electroencephalogram, etc.

In the embodiment of the present application, the first total early warning score or the second total early warning score can be obtained by means of a plurality of scoring criteria such as an early warning score (EWS) and a modified early warning score (MEWS). The EWS, also the modified early warning score (MEWS), mainly involves assigning corresponding scores to a plurality of commonly used physiology indexes such as body temperature (Temp), systolic blood pressure (BP-S), heart rate (HR), respiration rate (RR), level of consciousness, blood oxygen (SpO2), and oxygen concentration (Supp.O2), and then using a statistical value of the scores to assess a clinical status or potential risk of a patient. Alternatively, the EWS in the embodiments of the present application may also refer to a pediatric early warning score (PEWS), etc., and which type of EWS or suitable population is not uniquely limited in the embodiments of the present application. A common method for determining the level of consciousness herein, such as a score based on LOC (AVPU), i.e., a state of consciousness is "AVPU" scoring. The scoring system divides the state of consciousness into four levels: alert, responsive to a (verba) stimuli, responsive to a pain stimuli, and non-responsive. A MEWS rule is used as an example below for explanation. MEWS has the characteristics of being simple to apply, easy to master, and fast and convenient to acquire clinical information, and is not limited by hardware device conditions of a hospital or an emergency department. It is widely applied in emergency work to accurately judge a patient's condition in time and better complete medical work. Patients in emergency clinical reception are graded according to the MEWS, and different treatment measures are taken according to the grade based on the total early warning score: (1) 0 to 5 point: the patient is in a stable condition and has no potential risk of critical illness, and therefore, the patient generally needs no hospitalization and can be diagnosed and treated according to general routine procedures; and in case of emergency, the treatment for this patient can be temporarily put on hold for later. (2) 5 to 8 points: the patient's condition is unstable and changes a lot, and there is a risk of suffering "potentially critical illness". An emergency physician should give priority to the patient for diagnosis and treatment, and notify the patient of the relevant situation in time, and arrange for the patient to be admitted to a specialist ward or even an ICU in a timely manner. (3) Above 9 points: the patient is critically ill, and has a significantly increased risk of death; and if conditions permitted, the patient should be immediately sent to an intensive care unit or a specialist ward for treatment. In addition, dynamic MEWS should be performed on patients. Patients with an individual score of 2 points are evaluated once every four hours, patients with an individual score of 3 points are evaluated once every two hours, patients with an individual score of 4 points are evaluated once every one hour, and a diagnosis and treatment plan is timely adjusted according to score changes. It can be seen that the distribution of each of the first total early warning scores or each of the second total early warning scores is determined by sub-scores respectively corresponding to the plurality of physiological parameters in the same time period.

Certainly, in one of the embodiments, different calculation rules may be used for the first total early warning score and the second total early warning score. Therefore, a plurality of physiological parameters corresponding to each first total early warning score may be different from or partially the same as a plurality of physiological parameters corresponding to each second total early warning score.

102. After at least one first total early warning score is acquired, the first frequency is adjusted to the second frequency if any one of the first total early warning scores is greater than or equal to a total score threshold. The greater the first total early warning score is, the higher the second frequency is.

In the embodiment of the present application, the greater the first total early warning score is, the higher the second frequency is; that is to say, if the first total early warning score acquired by the monitoring device is not less than the total score threshold, the acquisition frequency can be adjusted, and the adjusted frequency can be determined according to the magnitude of the first total early warning score.

Specifically, the magnitude of the first total early warning score can be measured by the magnitude of a numerical value. For example, when the first total early warning score has a numerical value variation range of 0 to 21, and the total score threshold is 14, the monitoring device or the monitor can adjust the first frequency to the second frequency when the first total early warning score is not less than 14. For example, acquiring the first total early warning score once every two hours is adjusted to acquiring the second total early warning score twice every two hours; still alternatively, acquiring the first total early warning score once every two hours is adjusted to acquiring the second total early warning score once every half an hour, etc. The specific values of the first frequency and the second frequency are not limited in the embodiment of the present application.

It can be understood that the above total score threshold may be set by the monitoring device or the monitor. For example, it may be initialized by a manufacturer when leaving a factory, or may be set according to different populations during use. If a patient is a child, a total score threshold may be set, and if a patient is an adult, another total score threshold may be set, i.e., the total score threshold may be set by the monitoring device or the monitor according to the population to which the patient belongs. Still alternatively, the total score threshold may also be manually set by medical staff, etc. How to set the total score threshold and how much the total score threshold is set to are not uniquely limited in the embodiment of the present application.

Based on the above description, referring to FIGS. 4A to 4F, FIGS. 4A to 4F are schematic diagrams of an interface for displaying a total early warning score provided according to an embodiment of the present application. FIGS. 4A to 4F specifically show total early warning scores displayed by the monitoring device or the monitor at 07:00 to 15:00. For example, the first frequency preset by the monitoring device or the monitor is once every two hours per acquiring of the first total early warning score; at 07:00, the monitoring device or the monitor acquires a first total early warning score, and if the first total early warning score is less than a total score threshold of 4, a first total early warning score may be acquired again at 09:00; at 09:00 and 11:00, the total early warning scores acquired by the monitoring device or the monitor are both less than 4. Therefore, the first total early warning score is still acquired once every two hours, i.e., at 13:00, a first total early warning score is acquired. After the acquisition, the monitoring device or the monitor detects that the first total early warning score is equal to the total score threshold of 4, and therefore, the monitoring device or the monitor adjusts the first frequency to the second frequency, i.e., the second total early warning score is collected in a way of acquiring the total early warning score once every one hour; and then the second total early warning score is acquired twice respectively at 14:00 and 15:00.

103. The total early warning scores obtained through calculation are sequentially output over time.

In one of the embodiments, the processor sequentially outputs the at least one first total early warning score and the at least one second total early warning score over time.

In the specific embodiment, the process of sequentially outputting the at least one first total early warning score and the at least one second total early warning score over time can be performed by using at least one of the following methods, which is specifically as follows.

The first method involves:

drawing a timeline in a trend graph region on a display interface of a monitoring device or a monitor display (also referred to as a display screen);

correspondingly outputting the at least one first total early warning score at at least one first position on the timeline to obtain at least one first icon;

correspondingly outputting the at least one second total early warning score at at least one second position on the timeline to obtain at least one second icon; and sequentially arranging the first and second icons over time on the timeline according to moments at which the corresponding at least one first total early warning score and at least one second total early warning score are respectively acquired.

Figure 4A:
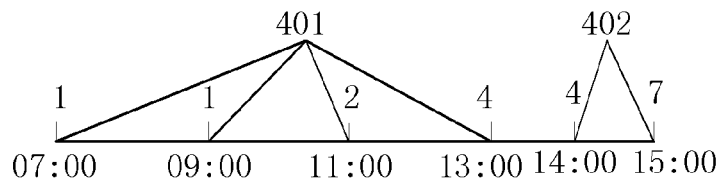
FIGS. 4A to 4F are schematic diagrams of an interface for displaying a total warning score provided according to an embodiment of the present application.
Figure 4B:
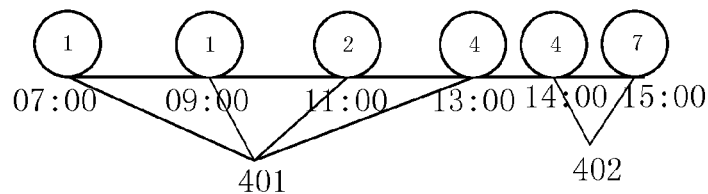
Figure 4C:
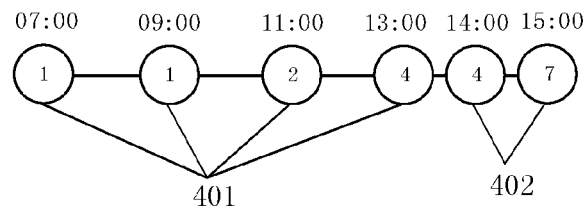
Figure 4D:
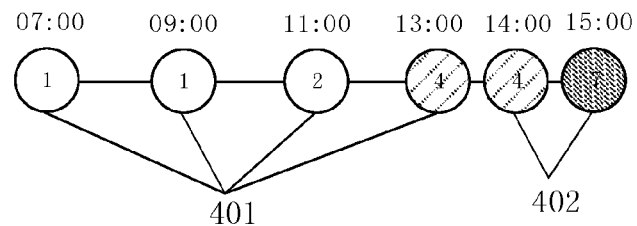
Figure 4E:
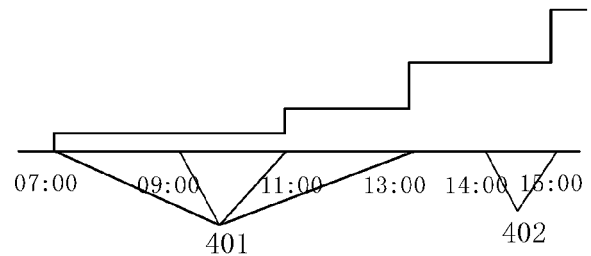
Figure 4F:
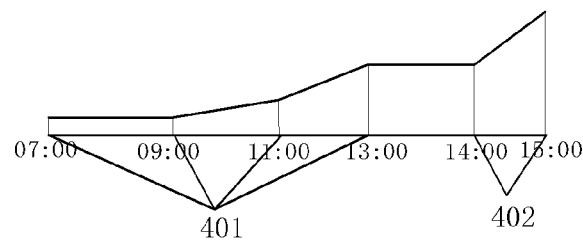

Specifically, the above first or second icons may be specific graphical icons (as shown in FIGS. 4B, 4C, and 4D), or may be straight lines (as shown in FIGS. 4E and 4F), or may be dots, or may be expressed in text (as shown in FIG. 4A). A trend change chart of corresponding historical total early warning scores can be obtained by displaying the first icons and the second icons. In addition, the display may display the historical total early warning scores in the form of a number axis shown in FIG. 4A; alternatively, the display may also display the historical total early warning scores in the form shown in FIG. 4B; alternatively, the display may also display the historical total early warning scores in the form shown in FIG. 4C; alternatively, the display may also display the historical total early warning scores in a way of distinguishing different total early warning scores as shown in FIG. 4D, so as to increase the effect of distinguishing different total early warning scores by a user; alternatively, the display may also display the historical total early warning scores in a stepped form shown in FIG. 4E; and still alternatively, the display may also display the historical total early warning scores in the form of broken lines shown in FIG. 4F, etc., and the way in which the display displays the total early warning scores of the object is not uniquely limited in the embodiment of the present application.

In addition, in one of the embodiments, in the above trend change chart, a distance interval between two adjacent first positions on the timeline is related to the first frequency, and a distance interval between two adjacent second positions on the timeline is related to the second frequency. For example, referring to FIGS. 4A to 4F, first total early warning scores of 1, 1, 2, and 4 are sequentially and correspondingly marked at first positions 401 respectively corresponding to 7:00, 9:00, 11:00, and 13:00; and second total early warning scores of 4 and 7 are sequentially and correspondingly marked at second positions 402 corresponding to 14:00 and 15:00. It can be seen that the corresponding time interval of the first total early warning scores is two hours (i.e., the first frequency), and the time interval of the second total early warning scores is one hour (i.e., the second frequency). Therefore, the adjacent intervals of the first positions on the timeline are related to the first frequency, and the adjacent intervals of the second positions on the timeline are related to the second frequency.

In addition, in one of the embodiments, when the first total early warning score or the second total early warning score is greater than or equal to the total score threshold, the corresponding first icon or second icon is highlighted. For example, referring to FIG. 4D, a first icon and a second icon drawn at a first position corresponding to 13:00 and second positions corresponding to 14:00 and 15:00 are highlighted. The way of highlighting in a distinguishing manner can be implemented by modifying an attribute value, such as a rendering color of an icon and a shape and size of an icon.

In addition, because each total early warning score originates from sub-scores corresponding to a plurality of physiological parameters, for example, the sub-scores corresponding to the plurality of physiological parameters can be summed up or weighted to obtain the total early warning score. Therefore, in some of the embodiments, the first total early warning scores or the second total early warning scores are respectively determined by sub-scores of a plurality of physiological parameters. Specifically, in one of the embodiments, the above method further comprises:

determining that each of the first total early warning scores and/or of the second total early warning scores has a sub-score of at least one physiological parameter that exceeds a sub-score threshold; and outputting prompt information indicating that each of the first total early warning scores and/or of the second total early warning scores has a sub-score of at least one physiological parameter that exceeds a sub-score threshold.

Figure 5A:
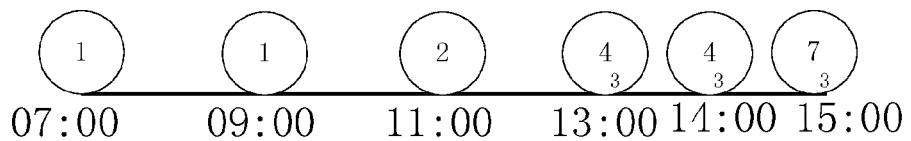
FIGS. 5A and 5B are schematic diagrams of an interface for displaying a total early warning score provided according to an embodiment of the present application.
Figure 5B:
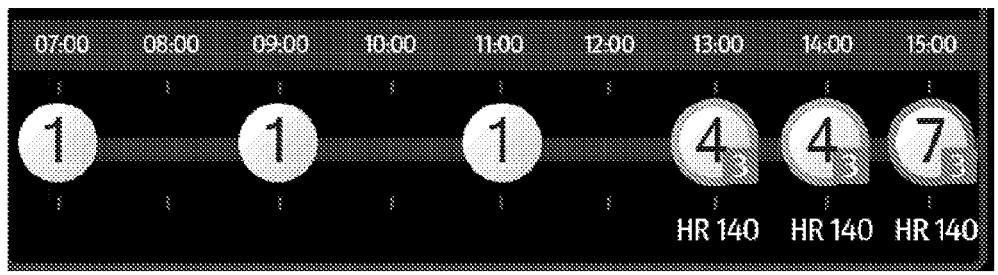

For example, referring to FIGS. 5A and 5B, FIGS. 5A and 5B are schematic diagrams of an interface for displaying total EWSes (comprising first total early warning scores and second total early warning scores) provided according to an embodiment of the present application. In FIGS. 5A and 5B, in a trend graph region, corresponding prompt information is displayed at a position related to the first total early warning score, and corresponding prompt information is displayed at a second position related to the second total early warning score. The prompt information comprises prompt information indicating that sub-scores in the first total early warning score or the second total early warning score exceed (are greater than or equal to) a sub-score threshold of 3. In FIG. 5B, the prompt is displayed and highlighted by means of marking the sub-score threshold of 3; alternatively, in FIG. 5A, the prompt is highlighted by marking a number of parameters, for which sub-scores in the first total early warning score or the second total early warning score exceed (are greater than or equal to) the sub-score threshold of 3. Therefore, in one of the embodiments, corresponding prompt information may be displayed in a trend graph region and at a position related to the first total early warning score and/or the second total early warning score; and the prompt information comprises at least one of the number of parameters, for which sub-scores in the first total early warning score or the second total early warning score exceed (are greater than or equal to) the sub-score threshold, the sub-score threshold, relevant physiological parameters, for which sub-scores in the first total early warning score or the second total early warning score exceed (are greater than or equal to) the sub-score threshold, etc. The prompt information being the relevant physiological parameters, for which sub-scores in the first total early warning score or the second total early warning score exceed (are greater than or equal to) the sub-score threshold is used as an example to explain that moments of 13:00, 14:00 and 15:00 in FIG. 5B respectively correspond to the marked "HR=140", and this means that in total early warning scores obtained at the moments of 13:00, 14:00 and 15:00, a special reminder is provided when a sub-score corresponding to the physiological parameter HR exceeds the sub-score threshold of 3.

The second method is as follows. sequentially outputting the at least one first total early warning score and the at least one second total early warning score over time is performed using the following display method:

drawing real-time status icons in a real-time refreshing region on the display interface;

sequentially assigning, in the first time period, numerical values corresponding to the at least one first total early warning score to display results of the real-time status icons over time; and sequentially assigning, in the second time period, numerical values corresponding to the at least one second total early warning score to display results of the real-time status icons over time.

Figure 6A:
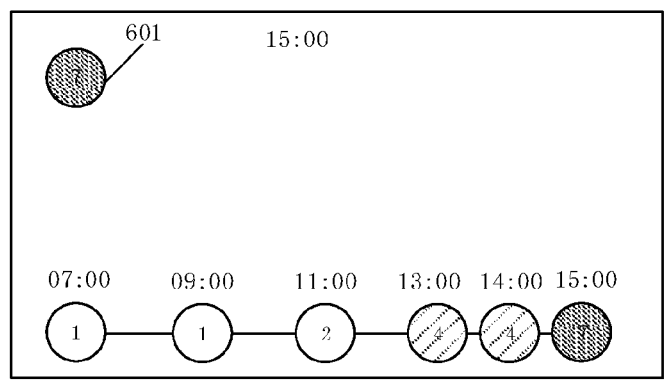
FIGS. 6A to 6E are schematic diagrams of an interface for displaying a total early warning score provided according to an embodiment of the present application.
Figure 6B:
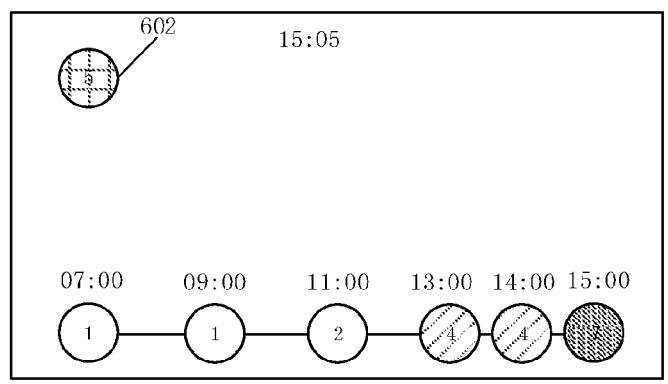
Figure 6C:
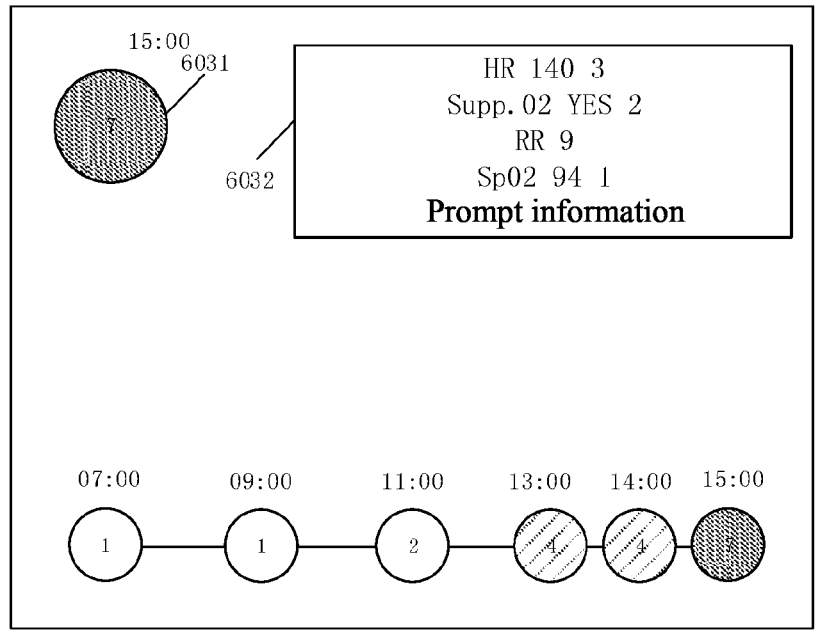
Figure 6D:
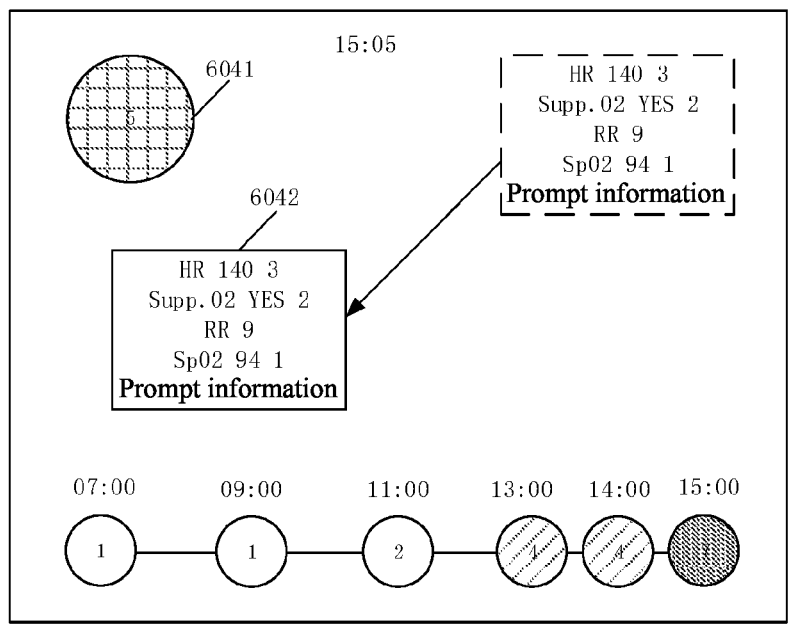
Figure 6E:
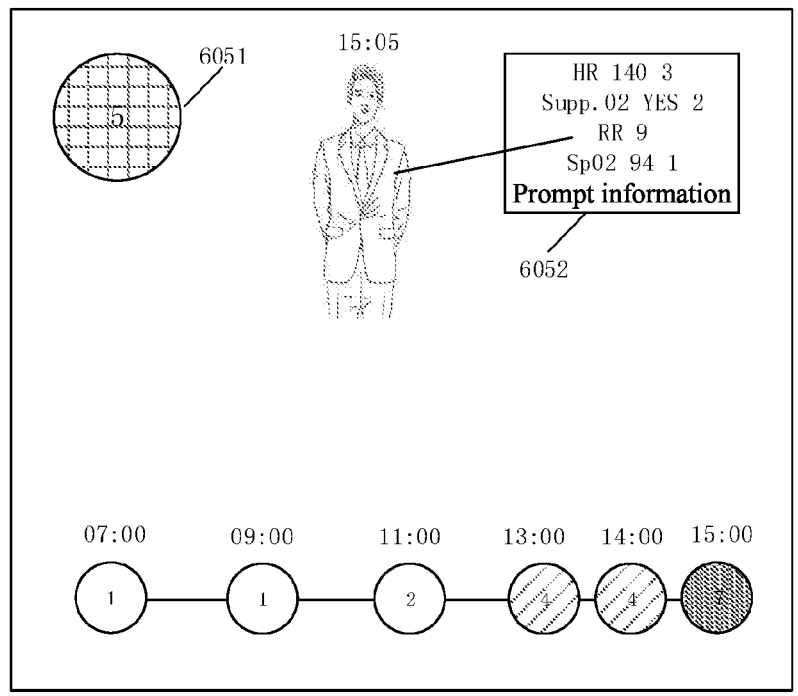

For example, as shown in FIGS. 6A to 6E, and FIGS. 7A, and 7B, a real-time status icon can be displayed by a specific icon, and a display result of the real-time status icon can be associated with the total early warning score by using a size of a circular icon, which is an icon 601 in the upper left corner of FIG. 6A, and 602 in the upper left corner of FIG. 6B, respectively. Alternatively, as shown in FIGS. 6C, 6D, and 6E, a text display result in the real-time status icon is associated with the total early warning score, which is 6031 and 6032 in FIG. 6C, 6041 and 6042 in FIG. 6D, and 6051 and 6052 in FIG. 6E, respectively. For another example, the real-time status icon may be displayed using the icon shown in a region 701 shown in FIG. 7A, and the icon shown in a region 702 shown in FIG. 7B.

For another example, in some embodiments, as shown in FIGS. 6A to 6E, when the first total early warning score or the second total early warning score is greater than or equal to the total score threshold, the real-time status icon is highlighted and rendered. The rendering can be distinguished by changing shape, size, color attributes, etc. of the real-time status icon. Certainly, still further, associated rendering attributes are determined according to a score range of the first or second total early warning scores. For example, when the first total early warning scores or the second total early warning scores are respectively in score ranges of different grades such as 0 to 4 points, 4 to 7 points, 7 to 14 points, and above 14 points, real-time status icons in different score ranges are distinguished by different rendering colors.

In some embodiments, it is determined that each of the first total early warning scores and/or each of the second total early warning scores has a sub-score of at least one physiological parameter that exceeds a sub-score threshold; and prompt information indicating that each of the first total early warning scores and/or each of the second total early warning scores has a sub-score of at least one physiological parameter that exceeds a sub-score threshold is output. For example, in FIGS. 6A to 6E, in the real-time refreshing region, corresponding first prompt information is sequentially displayed when in the first time period according to a moment at which the corresponding at least one first total early warning score is acquired, and corresponding second prompt information is sequentially displayed when in the second time period according to a moment at which the corresponding at least one second total early warning score is acquired. The prompt information herein may be "HR 140 3; Supp.O2 YES 2; RR 9; SpO2 94 1; prompt information" in FIGS. 6C to 6E.

Figure 7A:
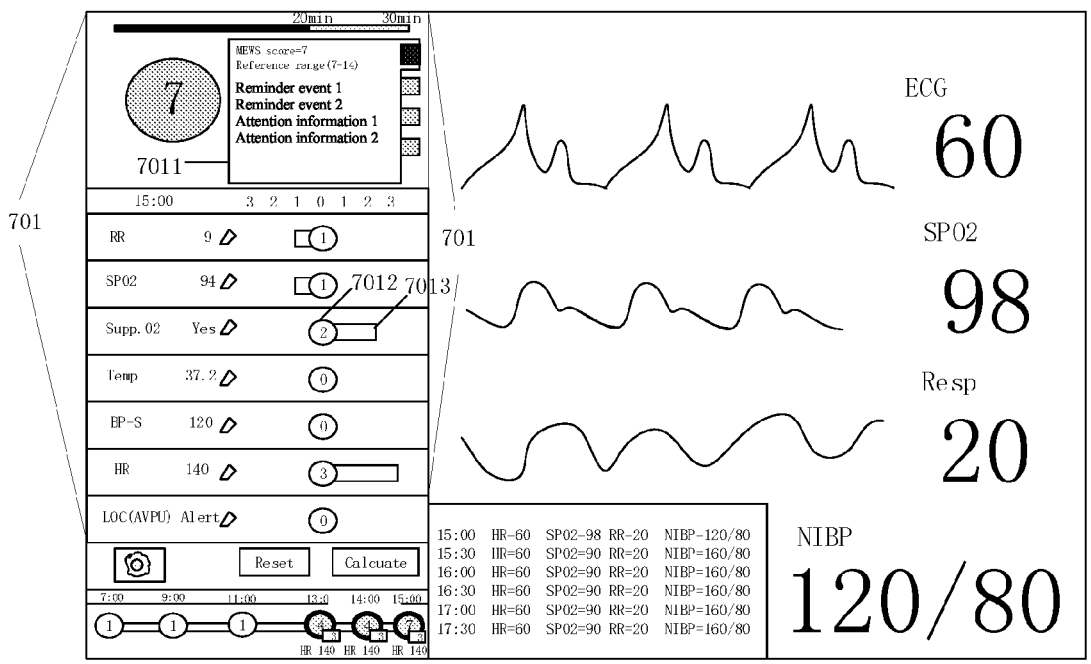
FIGS. 7A and 7B are schematic diagrams of an interface for displaying a total early warning score provided according to an embodiment of the present application.

Still further, as shown in FIG. 7A, a plurality of sub-score display icons 7012 can be drawn in a real-time refreshing region 701 on a display interface, and each sub-score display icon is associated with one physiological parameter. For example, FIG. 7A shows such physiological parameters as body temperature (Temp), systolic blood pressure (BP-S), heart rate (HR), respiration rate (RR), blood oxygen (SpO2), and oxygen concentration (Supp.O2), real-time values of which are respectively body temperature (Temp)=37.2, systolic blood pressure (BP-S)=120, heart rate (HR)=140, respiration rate (RR)=9, blood oxygen (SpO2)=94, and oxygen concentration (Supp.O2)=YES. In the first time period, sub-scores corresponding to relevant physiological parameters in the first total early warning score are sequentially assigned to display results of the sub-score display icons over time; and in the second time period, sub-scores corresponding to relevant physiological parameters in the second total early warning score are sequentially assigned to display results of the sub-score display icons over time. As shown in FIG. 7A, a display result of each of the sub-score display icons is displayed in the form of a columnar bar, a length of a columnar bar 7013 is associated with a numerical value of a relevant sub-score, and an orientation of the columnar bar reflects a change trend of the relevant sub-score with respect to a reference threshold. The reference threshold herein is sub-score=0. A single physiological parameter has 7 segments of high 3 points, 0 point, and low 3 points, which are respectively low 3 points (red), low 2 points (orange), low 1 point (yellow), zero point (white), high 1 point (yellow), high 2 points (orange), and high 3 points (red). Different numerical values of each physiological parameter correspond to different score segments, lengths of the columnar bars correspond to different score segments, and colors of the columnar bars correspond to different score segment colors. A horizontal columnar bar is used in the interface to indicate a score segment of a single physiological parameter. The longer the columnar bar is, the higher the sub-score is. For example, if the heart rate (HR) is less than or equal to 40, the parameter is low 2 points, and the columnar bar is leftward; if the heart rate (HR) is between 111 and 129, the parameter is high 2 points and the columnar bar graph is rightward; and the value of each physiological parameter is displayed in the center. The orientation of the columnar bar is used to reflect whether a relevant sub-score is higher or lower with respect to the reference threshold of 0.

In some embodiments, it is not necessary for all of a plurality of physiological parameters that determine the first total early warning score or the second total early warning score to be displayed in the real-time refreshing region. The plurality of sub-score display icons correspond to a part of parameters of a plurality of physiological parameters used to determine the first total early warning score or the second total early warning score, wherein sub-scores respectively corresponding to the part of parameters exceed a sub-score threshold. This can reduce the size of the display space on the interface, so as to highlight key points.

In addition, in some embodiments, the number of times the first total early warning score or the second total early warning score is not less than the total score threshold is output and displayed on the display interface.

Referring to FIG. 7A, in some embodiments, associated status attention prompt information is determined according to a score range of the first or second total early warning score; a prompt information attribute page is drawn in a real-time refreshing region on a display interface; and the status attention prompt information is output on the prompt information attribute page 7011. The status attention information herein comprises information regarding corresponding reminder and attention items in the score range of respective total early warning scores, information indicating the score range of scores, etc.

Referring to FIG. 7A, an associated rendering attribute is determined according to a score range of the first or second total early warning score; and a display effect of the prompt information attribute page is adjusted according to the rendering attribute.

Figure 7B:
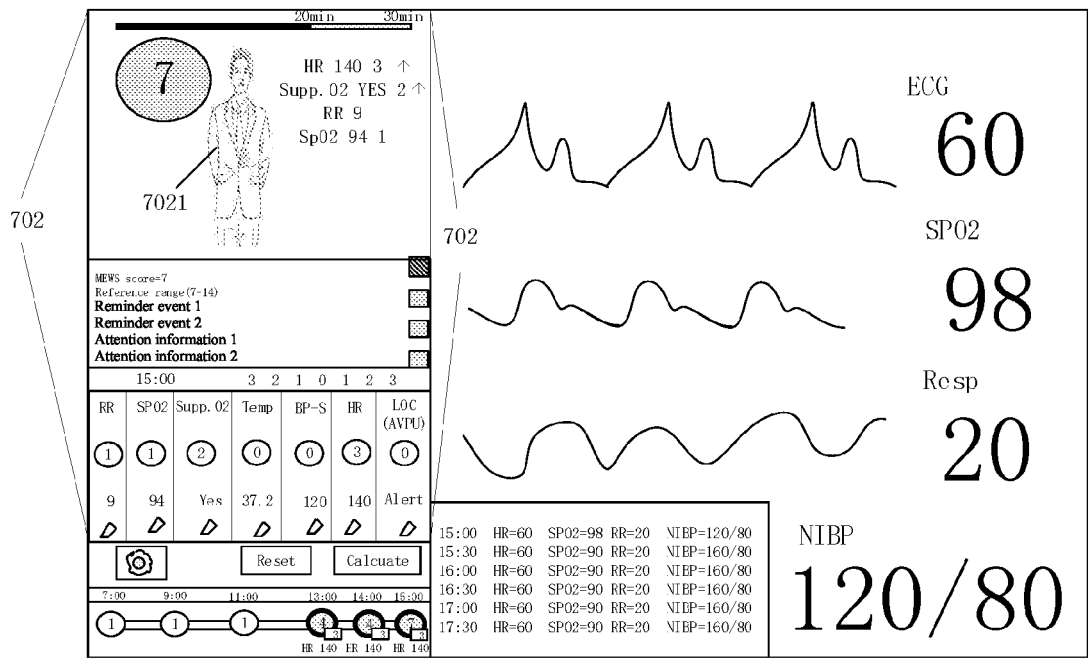

Referring to FIG. 7B, a pictogram icon 7021 is drawn in a real-time refreshing region on a display interface, wherein the pictogram icon is similar to a shape of the object that is monitored in real time; and association marking is performed on physiological parameters contained in the prompt information and the pictogram icon.

The implementation of the embodiments of the present application can make it possible to display both a first total early warning score acquired at a first frequency and a second total early warning score acquired at a second frequency; moreover, the second total early warning score acquired at the second frequency is greater than the first total early warning score acquired at the first frequency, which can clearly notify medical staff of a patient's physical changes within a preset duration, thereby effectively avoiding the need for the medical staff to manually make correspondence of historical numerical values by themselves in urgent need of relevant numerical values (such as a total EWS), and thus improving the working efficiency of the medical staff, and making it possible to significantly improve, in a timely manner, the medical staff's attention to the patient's physical condition and thus improving the monitoring efficiency of a monitoring device or a monitor.

Figure 8:
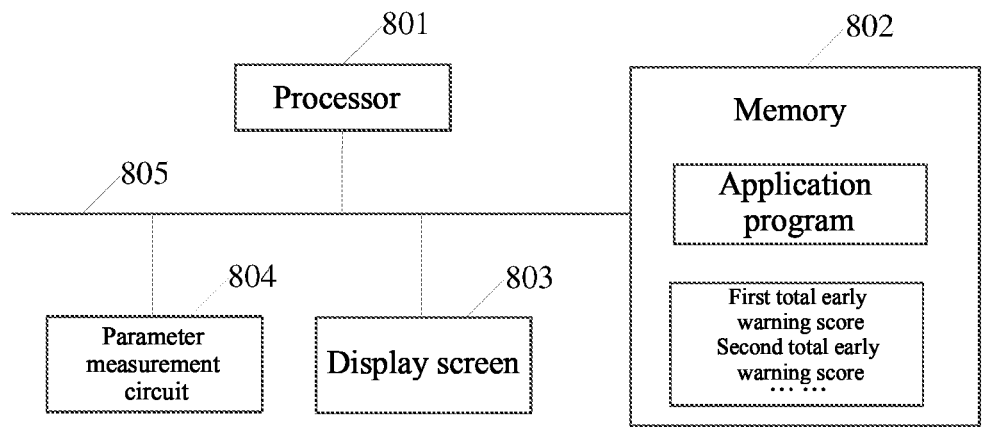
FIG. 8 is a schematic structural diagram of a monitoring device provided according to an embodiment of the present application.

Referring to FIG. 8, FIG. 8 is a schematic structural diagram of a monitoring device provided according to an embodiment of the present application. As shown in FIG. 8, the monitoring device may comprise: a processor 801, a memory 802, a display screen 803, and a parameter measurement circuit 804. The processor 801, the memory 802, the display screen 803, and the parameter measurement circuit 804 can be connected to each other by means of a connecting line 805. The connecting line may comprise a transmission line or a bus, etc., and the specific type of the connecting line is not limited in the embodiment of the present application.

The parameter measurement circuit 804 may be configured to be electrically connected to a sensor accessory provided on the body of a patient, and is configured to obtain a plurality of physiological parameters.

The memory 802 comprises, but is not limited to, a random access memory (RAM), a read-only memory (ROM), an erasable programmable read-only memory (EPROM or a flash memory), or a portable read-only memory (CD-ROM), etc.

The processor 801 may be one or more central processing units (CPU for short). When the processor 801 is one CPU, the CPU may be a single-core CPU or a multi-core CPU. Alternatively, the processor may also be another type of processor, etc., and the type of the processor is not limited in the embodiment of the present application.

The memory 802 is configured to store a computer program which comprises program instructions, and the processor 801 is configured to execute the program instructions stored in the memory 802. The processor 801 is configured to invoke the program instructions to:

receive a plurality of physiological parameters collected, in a first time period, from an object that is monitored in real time, so as to obtain a first set of physiological data; acquire at least one first total early warning score at a first frequency based on the first set of physiological data; receive a plurality of physiological parameters collected, in a second time period, from the object that is monitored in real time, so as to obtain a second set of physiological data; acquire at least one second total early warning score at a second frequency based on the second set of physiological data; and sequentially output the at least one first total early warning score and the at least one second total early warning score over time.

Optionally, the first time period is neither the same as nor overlaps with the second time period.

Optionally, each of the first total early warning scores or each of the second total early warning scores is determined by sub-scores respectively corresponding to the plurality of physiological parameters in the same time period.

Optionally, the second frequency is different from the first frequency.

Optionally, the processor 801 is further configured to adjust the first frequency to the second frequency if any one of the first total early warning scores is greater than or equal to a total score threshold, wherein the greater the first total early warning score is, the higher the second frequency is.

Optionally, the processor 801 is specifically configured to: draw a timeline in a trend graph region on a display interface; and correspondingly output the at least one first total early warning score at at least one first position on the timeline to obtain at least one first icon; and correspondingly output the at least one second total early warning score at at least one second position on the timeline to obtain at least one second icon; and sequentially arrange the first and second icons over time on the timeline according to moments at which the corresponding at least one first total early warning score and at least one second total early warning score are respectively acquired.

It can be understood that the processor 801 may further be configured to control the display screen 803 to output the first total early warning score, the second total early warning score, etc.

Optionally, the processor 801 is specifically configured to: draw real-time status icons in a real-time refreshing region on the display interface; and sequentially assign, in the first time period, numerical values corresponding to the at least one first total early warning score to display results of the real-time status icons over time; and sequentially assign, in the second time period, numerical values corresponding to the at least one second total early warning score to display results of the real-time status icons over time.

Optionally, a distance interval between two adjacent first positions on the timeline is related to the first frequency, and a distance interval between two adjacent second positions on the timeline is related to the second frequency.

Optionally, when the first total early warning score or the second total early warning score is greater than or equal to a total score threshold, the corresponding first icon or second icon is highlighted.

Optionally, when the first total early warning score or the second total early warning score is greater than or equal to a total score threshold, the real-time status icon is highlighted and rendered.

Optionally, the processor 801 is further configured to: determine that each of the first total early warning scores and/or each of the second total early warning scores has a sub-score of at least one physiological parameter that exceeds a sub-score threshold; and output prompt information indicating that each of the first total early warning scores and/or each of the second total early warning scores has a sub-score of at least one physiological parameter that exceeds a sub-score threshold.

It can be understood that the processor 801 may further be configured to control the display screen 803 to output prompt information indicating that each of the first total early warning scores and/or each of the second total early warning scores has a sub-score of at least one physiological parameter that exceeds a sub-score threshold.

Optionally, the processor 801 is further configured to: display the corresponding prompt information in the trend graph region and at a position(s) related to the first total early warning score and/or the second total early warning score; or in the real-time refreshing region, sequentially display corresponding first prompt information when in the first time period according to a moment at which the corresponding at least one first total early warning score is acquired, and sequentially display corresponding second prompt information when in the second time period according to a moment at which the corresponding at least one second total early warning score is acquired.

It can be understood that the processor may further be configured to control the display screen to display prompt information, first prompt information, second prompt information, etc.

Optionally, the processor is further configured to: draw a plurality of sub-score display icons in a real-time refreshing region on a display interface, wherein each of the sub-score display icons is associated with one physiological parameter; and sequentially assign, in the first time period, sub-scores corresponding to relevant physiological parameters in the first total early warning score to display results of the sub-score display icons over time; and sequentially assign, in the second time period, sub-scores corresponding to relevant physiological parameters in the second total early warning score to display results of the sub-score display icons over time.

Optionally, the plurality of sub-score display icons correspond to a part of parameters of a plurality of physiological parameters used to determine the first total early warning score or the second total early warning score, wherein sub-scores respectively corresponding to the part of parameters exceed a sub-score threshold.

Optionally, the processor is further configured to output and display the number of times the first total early warning score or the second total early warning score is not less than the total score threshold.

Optionally, the processor is further configured to: determine associated status attention prompt information according to a score range of the first or second total early warning score; draw a prompt information attribute page in a real-time refreshing region on a display interface; and output the status attention prompt information on the prompt information attribute page.

Optionally, the processor is further configured to: determine an associated rendering attribute according to a score range of the first or second total early warning score; and adjust a display effect of the prompt information attribute page according to the rendering attribute.

Optionally, the processor is further configured to: draw a pictogram icon in the real-time refreshing region on the display interface, wherein the pictogram icon is similar to a shape of the object that is monitored in real time; and perform association marking on physiological parameters contained in the prompt information and the pictogram icon.

Optionally, a display result of each of the sub-score display icons is displayed in the form of a columnar bar, a length of the columnar bar is associated with a numerical value of a relevant sub-score, and an orientation of the columnar bar reflects a change trend of the relevant sub-score with respect to a reference threshold.

It can be understood that in the embodiment of the present application, the processor may further be configured to control the display screen to display related information, etc., which will not be described in detail here.

In a specific implementation, the processor 801 and the display screen 803 described in the embodiment of the present application may be configured to execute the implementation of FIG. 4 described in the embodiment of the present application, which will not be repeated here.

Specifically, an embodiment of the present application further provides a computer-readable storage medium, storing a computer program, wherein the computer program comprises program instructions, and when the program instructions are executed by a processor, the following steps are implemented:

receiving a plurality of physiological parameters collected, in a first time period, from an object that is monitored in real time, so as to obtain a first set of physiological data; acquiring at least one first total early warning score at a first frequency based on the first set of physiological data; receiving a plurality of physiological parameters collected, in a second time period, from the object that is monitored in real time, so as to obtain a second set of physiological data; acquiring at least one second total early warning score at a second frequency based on the second set of physiological data; and sequentially outputting the at least one first total early warning score and the at least one second total early warning score over time.

It can be understood that the computer-readable storage medium may be an internal storage unit of the monitoring device described in any of the above embodiments, such as a hard disk or an internal memory of the monitoring device. The computer-readable storage medium may also be an external storage device of the monitoring device, such as a removable hard disk, a smart media card (SMC), a secure digital (SD) card, and a flash card equipped on the monitoring device. Further, the computer-readable storage medium may further comprise both an internal storage unit and an external storage device of the monitoring device. The computer-readable storage medium is configured to store the computer program and other programs and data required by the monitoring device. The computer-readable storage medium may further be configured to temporarily store data that has been or will be output.

Figure 9:
FIG. 9 is a schematic diagram of the architecture of a display system provided according to an embodiment of the present application.

Referring to FIG. 9, FIG. 9 is a display system provided according to an embodiment of the present application. The display system comprises: a monitor (such as a bedside monitor 212) and a portable monitoring device 213.

The monitor (such as the bedside monitor 212) is communicatively connected to the portable monitoring device 213, such as in a wireless manner, or in a wired manner, etc., which is not limited in the embodiment of the present application.

As shown in FIG. 9, the monitor 901 is communicatively connected to the portable monitoring device 902 to implement data interaction. For example, when the monitor 901 displays a first total early warning score and a second total early warning score, the portable monitoring device 902 can also display the first total early warning score and the second total early warning score, such that a user can learn about physical changes of a patient, etc. by viewing the portable monitoring device 902 worn by the patient, without needing to pay attention to the monitor all the time.

It can be understood that for specific implementations of the monitor and the portable monitoring device, reference may be made to the above embodiments, which will not be described in detail here.

Modules or units in all the embodiments of the present application can be implemented by a general-purpose integrated circuit, such as a CPU, or by an application specific integrated circuit (ASIC).

It should be noted that, for brevity, the foregoing method embodiments are described as a series of action combinations. However, a person skilled in the art should understand that the present application is not limited to the described action order, because according to the present application, some steps may adopt another order or occur simultaneously. Moreover, a person skilled in the art should also understand that the embodiments described in the specification all belong to preferred embodiments, and the involved actions and modules are not necessarily required by the present application.

According to actual requirements, the order of the steps in the method in the embodiments of the present application may be adjusted, or the steps may be combined or omitted.

Those of ordinary skill in the art can understand that all or some of the procedures of the methods in the above embodiments can be implemented by a computer program instructing related hardware. The program may be stored in a computer-readable storage medium, and the program, when executed, may comprise the procedures of the embodiments of the methods described above. The storage medium may be a magnetic disk, an optical disk, a read-only memory (ROM), or a random access memory (RAM for short), etc.

The invention claimed is:

1. A method for displaying an early warning score by a patient monitoring device, the method comprising:
   receiving, in a first time period, a plurality of physiological parameters collected by a sensor accessory from an object that is monitored in real time, so as to obtain a first set of physiological data:
   calculating, by a processor of the patient monitoring device, at least one first total early warning score at a first frequency based on the first set of physiological data;
   switching from the first time period to a second time period and increasing from the first frequency at which the calculating is performed by the processor to a second frequency at which the calculating is performed by the processor when any one of the first total early warning scores is determined, by the processor, to be greater than or equal to a total score threshold;
   receiving, in the second time period, a plurality of physiological parameters collected by the sensor accessory from the object that is monitored in real time, so as to obtain a second set of physiological data;
   calculating, by the processor of the patient monitoring device, at least one second total early warning score at the second frequency based on the second set of physiological data;
   outputting, on a display screen of the patient monitoring device, the at least one first total early warning score at the first frequency during the first time period, followed by outputting the at least one second total early warning score at the second frequency during the second time period, wherein;
      each of the first total early warning scores or each of the second total early warning scores is determined by sub-scores respectively corresponding to the plurality of physiological parameters in a same time period;
      the sub-scores corresponding to one of the plurality of physiological parameters comprise multiple score segments and each score segment corresponds to different numerical value ranges of the physiological parameter; and
      the score segments comprise one or more high score segments and one or more low score segments; and
   displaying a plurality of sub-score display icons on the display screen, wherein each of the sub-score display icons is associated with one physiological parameter, wherein a display result of the sub-score display icon is displayed in the form of a columnar bar wherein:
      a length of the columnar bar is associated with a numerical value of a relevant sub-score. an orientation of the columnar bar reflects a change trend of the relevant sub-score with respect to a reference threshold, and a first orientation of the columnar bar corresponds to the high score segment and a second orientation of the columnar bar opposite to the first orientation corresponds to the low score segment.

2. The method of claim 1, wherein the first time period is neither the same as nor overlaps with the second time period.

3. The method of claim 1, wherein the second frequency is different from the first frequency.

4. The method of claim 1, wherein a greater first total early warning score corresponds to a higher second frequency.

5. The method of claim 1, wherein outputting the at least one first total early warning score at the first frequency during the first time period, followed by displaying the at least one second total early warning score at the second frequency during the second time period comprises:
   displaying a timeline in a trend graph region on the display screen;
   sequentially outputting the at least one first total early warning score as at least one first icon at at least one first position on the timeline corresponding to moments at which the at least one first total early warning score are determined in the first time period; and
   sequentially outputting the at least one second total early warning score at at least one second position as at least one second icon on the timeline corresponding to moments at which the at least one second total early warning score are determined in the second time period, wherein the at least one second position is subsequent to the at least one first position on the timeline.

6. The method of claim 5, wherein a distance between two adjacent first positions on the timeline is related to the first frequency, a distance between two adjacent second positions on the timeline is related to the second frequency, and the distance between two adjacent first positions is larger than the distance between two adjacent second positions.

7. The method of claim 5, further comprising: when the first total early warning score or the second total early warning score is greater than or equal to a total score threshold, highlighting the corresponding first icon or second icon.

8. The method of claim 5, further comprising:
   determining that each of the first total early warning scores or each of the second total early warning scores has a sub-score of at least one physiological parameter that exceeds a sub-score threshold;

outputting prompt information indicating that each of the first total early warning scores or each of the second total early warning scores has a sub-score of at least one physiological parameter that exceeds a sub-score threshold; and displaying the corresponding prompt information in the trend graph region at one or more positions related to the first total early warning score or the second total early warning score.

9. The method of claim 1, wherein sequentially outputting the at least one first total early warning score and the at least one second total early warning score over time comprises:

drawing real-time status icons in a real-time refreshing region on the display screen;

in the first time period, sequentially assigning numerical values corresponding to the at least one first total early warning score to display results of the real-time status icons; and in the second time period, sequentially assigning, numerical values corresponding to the at least one second total early warning score to display results of the real-time status icons.

10. The method of claim 9, wherein when the first total early warning score or the second total early warning score is greater than or equal to a total score threshold, the real-time status icon is highlighted and rendered.

11. The method of claim 9, wherein the method further comprises:

outputting prompt information indicating that each of the first total early warning scores or each of the second total early warning scores that exceeds a total score threshold; and in the real-time refreshing region, sequentially displaying corresponding first prompt information in the first time period according to a moment at which the corresponding at least one first total early warning score is acquired, and sequentially displaying corresponding second prompt information in the second time period according to a moment at which the corresponding at least one second total early warning score is acquired.

12. The method of claim 9, wherein the method further comprises:

displaying a pictogram icon in a real-time refreshing region on the display screen, wherein the pictogram icon is similar to a shape of the object that is monitored in real time; and performing association marking on physiological parameters contained in the prompt information and the pictogram icon.

13. The method of claim 1, wherein the method further comprises:

in the first time period, sequentially assigning, sub-scores corresponding to relevant physiological parameters in the first total early warning score to display results of the sub-score display icons over time; and in the second time period, sequentially assigning, sub-scores corresponding to relevant physiological parameters in the second total early warning score to display results of the sub-score display icons over time.

14. The method of claim 13, wherein the plurality of sub-score display icons correspond to a part of a plurality of physiological parameters used to determine the first total early warning score or the second total early warning score, wherein sub-scores respectively corresponding to the part of said parameters exceed a sub-score threshold.

15. The method of claim 1, wherein the method further comprises:

outputting and displaying a number of times that the first total early warning score or the second total early warning score is not less than a total score threshold.

16. The method of claim 1, wherein the method further comprises:

determining associated status attention prompt information according to a score range of the first or second total early warning score;

displaying a prompt information attribute page in a real-time refreshing region on the display screen; and outputting the status attention prompt information on the prompt information attribute page.

17. The method of claim 16, wherein the method further comprises:

determining an associated rendering attribute according to a score range of the first or second total early warning score; and adjusting a display effect of the prompt information attribute page according to the rendering attribute.

18. A monitoring device, comprising:

a parameter measurement circuit, which is electrically connected to a sensor accessory provided on a body of a patient, and is configured to acquire a plurality of physiological parameters; and a processor, a display screen, and a memory, wherein the memory is configured to store a computer program, and the processor is configured to implement the following steps when executing the computer program stored in the memory;

receiving in a first time period, a plurality of physiological parameters collected, from the patient that is monitored in real time, so as to obtain a first set of physiological data;

calculating at least one first total early warning score at a first frequency based on the first set of physiological data;

receiving in a second time period subsequent to the first time period, a plurality of physiological parameters collected, from the patient that is monitored in real time, so as to obtain a second set of physiological data;

calculating at least one second total early warning score at a second frequency based on the second set of physiological data; and displaying a plurality of sub-score display icons on the display screen, wherein each of the sub-score display icons is associated with one physiological parameter, wherein a display result of the sub-score display icon is displayed in the form of a columnar bar, wherein a first orientation of the columnar bar corresponds to the high score segment and a second orientation of the columnar bar opposite to the first orientation corresponds to the low score segment, wherein the display screen is configured to output the at least one first total early warning score at the first frequency during the first time period, and then output the at least one second total early warning score at the second frequency during the second time period, wherein the at least one first total early warning score and the at least one second early warning score are displayed in a trend graph region on the display screen, and the at least one first total early warning score and the at least one second early warning score are sequentially displayed along a single timeline to indicate physical changes of the patient, and a distance between two first total early warning scores on the timeline is related to the first frequency, a distance between two second total early warning scores on the timeline is related to the second frequency, and the distance between the two first early warning scores is larger than the distance between the two second early warning scores.

19. The method of claim 1, wherein each score segment is provided with a preset score segment color;
  when the column bar is a horizontal columnar bar, the orientation of the horizontal columnar bar is leftward corresponding to the low score segment, the orientation of the horizontal columnar bar is rightward corresponding to the high score segment, current sub-score of the physiological parameter is displayed in a center, and a color of the horizontal columnar bar corresponds to the preset score segment color.

* * * * *